United States Patent [19]
Collins

[11] Patent Number: 6,155,989
[45] Date of Patent: Dec. 5, 2000

[54] VACUUM ENHANCED CUTANEOUS BIOPSY INSTRUMENT

[75] Inventor: Joseph Collins, St. Petersburg, Fla.

[73] Assignee: The United States of America as represented by the United States Department of Energy, Washington, D.C.

[21] Appl. No.: 09/339,915

[22] Filed: Jun. 25, 1999

[51] Int. Cl.⁷ ..................................................... A61B 5/00
[52] U.S. Cl. .......................................................... 600/565
[58] Field of Search ........................... 600/562, 564–567; 606/167, 170, 171, 184

[56] References Cited

U.S. PATENT DOCUMENTS

| | | | |
|---|---|---|---|
| 3,515,128 | 6/1970 | McEvoy | 600/566 |
| 4,796,623 | 1/1989 | Krasher et al. | 600/565 |
| 6,007,496 | 12/1999 | Brannon | 600/565 |

*Primary Examiner*—Max Hindenburg
*Attorney, Agent, or Firm*—Armand McMillan; Dickson G. Kehl; William R. Moser

[57] ABSTRACT

A syringe-like disposable cutaneous biopsy instrument equipped with a tubular blade at its lower end, and designed so that a vacuum is created during use, said vacuum serving to retain undeformed a plug of tissue cut from a patient's skin.

1 Claim, 1 Drawing Sheet

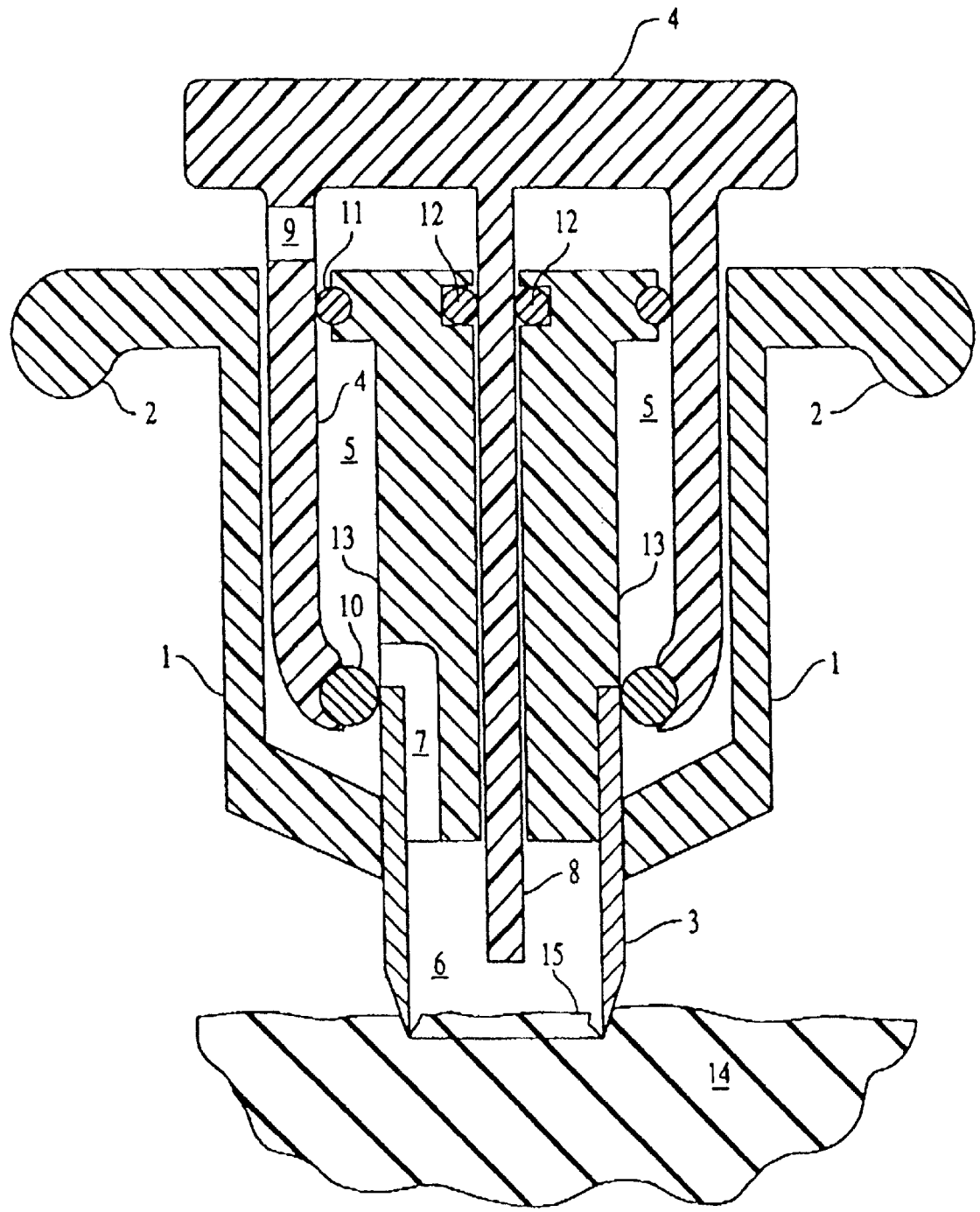

VACUUM ENHANCED CUTANEOUS BIOPSY INSTRUMENT

The United States Government has rights in this invention pursuant to Contract No. DE-AC04-92AL73000 between the U.S. Department of Energy and the Martin Marietta Specialty Components, Inc.

FIELD OF THE INVENTION

The invention relates to a disposable cutaneous biopsy instrument. More particularly, it relates to an instrument which can lift the biopsy specimen and facilitate its separation from the surrounding tissue.

DESCRIPTION OF THE PRIOR ART

Cutaneous biopsy instruments in current use separate the step of cutting of the sides of the incision from the step of lifting the tissue specimen or tissue plug in preparation for the lateral incision that removes the plug from the patient. After the round incision is made and the blade removed, the plug stays behind in the patient. The physician must then lift the plug high enough to allow a final lateral cut to effect complete removal. Since the only instruments available for this lifting operation are tweezer-like, the plug becomes grossly deformed and difficult to cut with accuracy. Since this causes problems for the laboratory, a larger plug is generally taken and subsequently trimmed to size. In addition, a relatively lengthy surgical procedure often leads to excess bleeding and creates subsequent additional trauma and discomfort.

Various approaches have been devised to solve some of the problems just reviewed. Those instruments often involved relatively complicated mechanical features such as the springs in U.S. Pat. No. 3,692,020 device.

U.S. Pat. No. 4,785,826 shows a device having a first hollow member and a second elongated hollow member within it. The second member has a flexible end portion including pointed segments which are normally opened to receive a tissue specimen but which can be mechanically closed (like grasping claws) to cut and capture a tissue specimen. A more recent instrument, disclosed in U.S. Pat. No. 5,857,981, involves a holder and a cutting member and a separate detachable specimen-retaining and retrieval device. U.S. Pat. Nos. 5,148,813 and 5,267,572 also disclose detachable retaining and retrieval devices.

It is, therefore, an object of this invention to provide a new, improved instrument for obtaining uniform cutaneous biopsy specimens. Another object is to provide an instrument that is easy to manufacture and use. Still another object is to provide a biopsy instrument that can produce a usable specimen by cutting a minimum area of tissue while causing little or no bleeding. Additional objects, advantages, and novel features of the invention will become apparent to those skilled in the art upon examination of the following description or may be learned in the practice of the invention.

SUMMARY OF THE INVENTION

The objects of the invention have been achieved by designing a new cutaneous biopsy instrument, somewhat similar to an hypodermic needle. It comprises an outer cylindrical body connected to an inner cylindrical body by a hollow tubular knife at their lower extremity. A cylindrical plunger is located between the outer and inner cylindrical bodies and can move up and down between two bodies. An annular chamber is located between the plunger and the inner cylindrical body and is connected to the empty space in the lower part of the tubular knife by a vent. Immediately before using the outer body of the instrument to insert the circular knife into the cutaneous tissue, the plunger is compressed, creating a vacuum. After insertion into the tissue, the volume above the tissue plug is exposed to this vacuum by further depression of the plunger. This transfer is audible, signaling the surgeon to discontinue depression and that the plug can be lifted. This lifting of the undeformed plug allows its separation with a scalpel, with no damage to surrounding tissue. Further depression of the plunger ejects the cutaneous plug into a proper receptacle.

BRIEF DESCRIPTION OF THE DRAWING

The drawing in this application is a cross-sectional view of the cutaneous biopsy instrument of the invention. The proportions of its various components have been altered in order to illustrate them more clearly.

DETAILED DESCRIPTION OF THE INVENTION

The instrument of the invention can best be described by viewing the accompanying drawing. It should be kept in mind that the actual instrument that the drawing illustrates is preferably shaped like a syringe in that it has a rather elongated body with a plunger handle at one end and a hollow tubular knife or blade at the other end.

Referring now to the drawing, it can be seen that the instrument is made of an outer cylindrical or tubular body 1 equipped with two finger grips 2 at its upper end and an inner cylindrical body 13 integrally connected to it. A hollow tubular plunger 4 is fitted between said outer and inner bodies, leaving annular chamber 5 which is connected to space 6 inside a hollow tubular blade 3 by means of vent 7. Another vent 9 in the upper part of plunger 4 allows trapped air to be expelled when the plunger is depressed during operation. A knock-out member 8 which is an integral part of plunger 4 protrudes from the top of said plunger through inner body 13 and ends in space 6 within hollow blade 3. O-rings or equivalent seals 10, 11, and 12 make possible the creation of a vacuum in spaces 5 and 6 during use of the instrument. A tissue sample 14 is shown under the biopsy instrument along with a cross-section of a tissue plug (to be biopsed) 15 cut into it within the interior the blade 3.

All the parts of this disposable instrument can be made of plastic, except for the metal blade, preferably of stainless steel, and the O-rings, preferably of rubber or other resilient material. Alternatively, integrally molded wiper-type (feathered) seals may be used.

During use, the outer body 1 allows the instrument to be positively held and manipulated. The plunger 4 is operated like a hypodermic needle. Here lies the uniqueness of the instrument: as the surgeon depresses the plunger, a vacuum is created in annular space 5 between the outer body 1 and the inner body 13. When the surgeon has established this vacuum, he takes the instrument to the surgical site and incises the round cut to the proper depth to form a tissue plug still attached to the tissue surface. When the tubular blade 3 is at the correct depth, the surgeon depresses the plunger the very short distance required to vent the chamber 6 adjacent to the plug into annular chamber 5 through vent 7. This causes the ambient pressure to keep plug 15 in the blade as the surgeon lifts the instrument. Detents or annular rings may be molded in (not shown). These can signal to the surgeon when the plunger movement must stop. The surgeon then can make an immediate lateral incision with a scalpel to separate the plug from the patient. The instrument is then removed from the surgical site and the plunger is depressed all the way so that knock-out member 8 can push the tissue plug into a proper container. The wound can then be quickly dressed before any significant hemorrhaging occurs.

Advantageously, the instrument makes it possible to hold the shape of the tissue plug as it is removed from the patient, thus permitting the removal of a smaller sample of tissue than would otherwise be required by the instruments of the art.

I claim:

1. A syringe-like cutaneous biopsy instrument comprising:
  a) an outer tubular body integrally connected to an inner cylindrical body, said outer body being provided with two finger grips at its upper end;
  b) a cylindrical plunger located within said outer tubular body, comprising a handle and a vent at its upper end;
  c) a tubular blade attached to the lower end of said outer body;
  d) a knock-out member integrally and centrally attached to said handle and protruding through said inner body as far as within the space in said tubular blade; and
  e) an annular space between a section of said plunger and said inner body, said space being connected by a vent through the lower end of the inner body to the space within the tubular blade;

wherein a vacuum is created in said cylindrical space when the plunger is depressed and suction to hold an incised tissue plug is created in the hollow blade by air escaping to said annular space through said vent when the plunger is pulled up.

* * * * *